(12) United States Patent
Peng et al.

(10) Patent No.: US 10,011,550 B2
(45) Date of Patent: Jul. 3, 2018

(54) METHOD FOR PREPARING HIGH-CONTENT CONJUGATED LINOLEIC ACID WITH VEGETABLE OIL

(71) Applicant: ZHEJIANG MEDICINE CO., LTD., XINCHANG PHARMACEUTICAL FACTORY, Xinchang, Zhejiang (CN)

(72) Inventors: Yongjian Peng, Zhejiang (CN); Xinde Xu, Zhejiang (CN); Bin Shao, Zhejiang (CN); Lihua Zhang, Zhejiang (CN)

(73) Assignee: ZHEJIANG MEDICINE CO., LTD. XINCHANG PHARMACEUTICAL FACTORY, Xinchang, Zhejiang (CN)

( * ) Notice: Subject to any disclaimer, the term of this patent is extended or adjusted under 35 U.S.C. 154(b) by 0 days.

(21) Appl. No.: 15/511,135

(22) PCT Filed: Sep. 17, 2015

(86) PCT No.: PCT/CN2015/089825
§ 371 (c)(1),
(2) Date: Mar. 14, 2017

(87) PCT Pub. No.: WO2016/041506
PCT Pub. Date: Mar. 24, 2016

(65) Prior Publication Data
US 2017/0275228 A1 Sep. 28, 2017

(30) Foreign Application Priority Data

Sep. 19, 2014 (CN) .................... 2014 1 0481938X

(51) Int. Cl.
| | |
|---|---|
| C07C 51/09 | (2006.01) |
| C11C 3/10 | (2006.01) |
| C11B 7/00 | (2006.01) |
| C07C 67/02 | (2006.01) |
| G01N 30/02 | (2006.01) |

(52) U.S. Cl.
CPC .............. *C07C 51/09* (2013.01); *C07C 67/02* (2013.01); *C11B 7/0058* (2013.01); *C11C 3/10* (2013.01); *C11B 7/0041* (2013.01); *G01N 30/02* (2013.01); *G01N 2030/027* (2013.01)

(58) Field of Classification Search
CPC ..... C11B 7/0041; C11B 7/0058; C07C 67/02; C07C 51/09; C11C 3/10; G01N 30/02; G01N 2030/027
See application file for complete search history.

(56) References Cited

U.S. PATENT DOCUMENTS

| | | | | |
|---|---|---|---|---|
| 4,277,413 A | * | 7/1981 | Logan .................. | C11B 7/0008 554/193 |
| 2003/0181522 A1 | * | 9/2003 | Strube ....................... | C11B 3/12 514/558 |

FOREIGN PATENT DOCUMENTS

| | | | | |
|---|---|---|---|---|
| CN | 1982326 A | | 6/2007 | |
| CN | 101016244 A | * | 8/2007 | ............. C07C 67/03 |
| CN | 101486951 A | * | 7/2009 | ............... C11B 3/10 |
| CN | 101921186 A | | 12/2010 | |
| CN | 102408333 A | | 4/2012 | |
| CN | 102433223 A | | 5/2012 | |
| WO | WO 2010103146 A1 | | 9/2010 | |

OTHER PUBLICATIONS

CN 101016244 (A), Wenzhong, L. W., et al., Method of preparing conjugated linolenate from plant oil, English translation, 10 pages (Year: 2007).*
CN 101486951 (A), Xianglin, H., et al., Method for separating oleate, linoleic acid, oleate and linoleate, English translation, 7 pages (Year: 2009).*
Zhang, Cuan et al.; "Study of Purification a—Linolenic Acid with the Silver Nitrate-Silica Gel", Ion Exchange and Adsorption, vol. 21, No. 1,Dec. 31, 2005 (Dec. 31, 2005), section 2.2.2.

* cited by examiner

*Primary Examiner* — Yate' K Cutliff
(74) *Attorney, Agent, or Firm* — Global IP Services; Tianhua Gu

(57) ABSTRACT

A method for preparing high-content conjugated linoleic acid (CLA) through purification of vegetable oil includes alcoholysis, purification and isomerization of vegetable oil. Alcoholysis is for preparing corresponding methyl ester or ethyl ester with glyceride; purification of methyl ester or ethyl ester is for obtaining methyl linoleate or ethyl linoleate of content over 85% through silver-based silica gel column chromatography; high-content CLA is obtained after alkali-catalyzed conjugation of methyl linoleate or ethyl linoleate, and CLA products are prepared as needed. This invention changes the status quo of preparing high-content CLA with safflower oil alone, expands sources of CLA, and develops an efficient technology for separation and purification of linoleic acid. The CLA obtained is of high purity and meets applications in pharmaceutical, health care products and other industries.

6 Claims, No Drawings

METHOD FOR PREPARING HIGH-CONTENT CONJUGATED LINOLEIC ACID WITH VEGETABLE OIL

CROSS REFERENCE TO RELATED PATENT APPLICATION

The present application is the US national stage of PCT/CN2015/089825 filed on Sep. 17, 2015, which claims the priority of the Chinese patent application No. 201410481938X filed on Sep. 19, 2014, which applications are incorporated herein by reference.

FIELD OF THE INVENTION

This invention involves a method for efficient separation and purification of linoleate and preparation of conjugated linoleic acid with vegetable oil, particularly a method for separation and purification of linoleate through silver-based silica gel column chromatography.

BACKGROUND OF THE INVENTION

Conjugated Linoleic Acid (CLA) is a conjugated diene isomer with the position and space of linoleic acid. 9c, 11t-CLA and 10t, 12c-CLA are two main active components. With the physiological mechanism that affects human health being gradually explained, CLA attracts more and more attention of the international food and pharmaceutical circles, and it has been determined that CLA is capable of combating cancer, preventing arteriosclerosis, losing weight, improving immunity, enhancing resistance of cells to free radicals and so on. Therefore, CLA has broad application prospect and huge market potential as a medicine, health food, functional food or food preservative, or in meat or feed industry.

It needs to prepare CLA by artificial means since there is almost no CLA in the nature. Natural triglyceride vegetable oil rich in linoleic acid is an important raw material for preparing CLA products. It is the best way to prepare high-purity and high-activity CLA through alkali-catalyzed conjugation and saponification with such vegetable oil.

At present, CLA is mainly produced with safflower oil (composition is shown in the table below) at home and abroad. This oil contains the most linoleic acid among all known plants. Its fatty acid composition is simple, containing about 5% and 3% of saturated C16:0 and C18:0 respectively, about 10% of unsaturated C18:1, up to 73-85% of linoleic acid, and almost no C18:3 and fatty acid with more carbon. Only the linoleic acid of C18:2 undergoes isomerization reaction and other fatty acids almost play no role during preparation of CLA through alkali isomerization. Therefore, CLA products can be directly prepared through conjugation with safflower oil featured by simple composition and low content of impurities.

| Fatty acid | Content (%) |
| --- | --- |
| Fatty acid below C14 (<C14) | <0.1 |
| Myristic acid (C14:0) | <1.0 |
| Palmitic acid (C16:0) | 2-10 |
| Palmitoleic acid (C16:1) | <0.5 |
| Stearic acid (C18:0) | 1-10 |
| Oleic acid (C18:1) | 7-12 |
| Linoleic acid (C18:2) | 55-81 |
| Linolenic acid (C18:3) | <0.1 |
| Arachidic acid (C20:0) | <0.5 |
| Arachidonic acid (C20:1) | <0.5 |
| Behenic acid (C22:0) | <0.5 |

Relatively speaking, content of linoleic acid is low, and impurity composition is complicated in other vegetable oils, particularly content of some impurities similar to linoleic acid in property is relatively high, such as oleic acid. Oleic acid is similar to linoleic acid in structure and property. For example, their boiling point differs by less than 1° C., and their melting point and polarity are approximate. They are only different in number of double bonds. There are no effective methods for separation and purification, and rectification, low temperature crystallization, extraction, conventional adsorption chromatography, supercritical extraction and other common technologies can not realize effective separation, which makes it difficult to obtain CLA products of content over 80%. Therefore, it can not be used for preparation of CLA. Low yield and high price of safflower oil leads to the contradiction of insufficient raw materials for production of CLA and inefficient use of the abundant vegetable oils.

Silver ions can form π-complex with double bonds of unsaturated fatty acid, so they have specific binding force with double bonds. The number, position and configuration of double bonds have direct effect on the strength of binding force. Silver ions are loaded or bonded onto the adsorbent and separated because of difference in acting force of fatty acid with different number of double bonds and silver ions on the adsorbent. Silica gel is a common adsorbent, and silver-based silica gel can be obtained by adding silica gel into silver nitrate aqueous solution of certain concentration after mixing, suction filtration, drying and activation. Silver-based silica gel column chromatography is a method for step-by-step separation of fatty acid through a series of eluents with different polarities with silver-based silica gel as stationary phase, and a simple, timesaving, efficient and industrialized liquid chromatography. Research on separation of related substances with silver-loaded silica gel column has been reported at home and abroad.

A method for separation of linoleic acid in safflower oil with silver-based silica gel is introduced in patent CN 101921186A. High-purity linoleic acid products are obtained with safflower oil after silver-based silica gel column chromatography, but glyceride is used as raw material in the patent, which is bad for enrichment of linoleic acid and greatly reduces the recovery rate while obtaining high-purity products. A method for purification of EPA with silver-based silica gel is introduced in U.S. Pat. No. 0,027,865. EPA products of content over 90% can be obtained through silver-based silica gel column chromatography after two-step urea inclusion of fish oil fatty acid, but recovery rate is greatly reduced by the two-step urea inclusion.

J. L. Guil-Guerrero et al. studied the effect of separation and purification of silver-based silica gel chromatography for polyunsaturated fatty acid, and mainly separated and purified fatty acid with degree of unsaturation more than 2 with samples rich in polyunsaturated fatty acid; Jianxia Guo et al. conducted preliminary purification for linoleic acid with safflower oil through urea inclusion to remove saturated and monounsaturated fatty acids, and separated polyunsaturated fatty acid with silver-based silica gel column to obtain linoleic acid of purity more than 95%; Noorul Jannah Zainuddin et al. conducted silver-based silica gel chromatographic separation with catfish oil after preliminary urea inclusion and purification, and separated linoleic acid of purity over 90% from polyunsaturated fatty acid, but recovery rate of linoleic acid was only 12.9% due to influence of preliminary purification.

El Hassan et al. separated EPA products of content more than 90% from microalgae and fish oil with silver-based silica gel; Sajilata et al. separated γ-linolenic acid of content over 96% from spirulina with silver-loaded silica gel column.

It can be seen from the above patents and literatures that separation and purification of fatty acid with silver-loaded silica gel column mainly have the following deficiencies at home and abroad: separation of polyunsaturated fatty acids is dominant, such as linolenic acid, EPA, etc., and there is no special research report on separation of fatty acid of low saturation, particularly separation of oleic acid and linoleic acid; the samples are subject to urea inclusion before separation to remove saturated and monounsaturated fatty acids in the few purification technologies for linolenic acid, which finally becomes separation of polyunsaturated fatty acid; the raw material used in the report is safflower oil or fatty acid subject to preliminary purification that contains a relatively high proportion of linoleic acid, failing to clearly show the role of silver-loaded silica gel in purification of linoleic acid, and recovery rate of final samples is very low due to pre-treatment; the raw material is glyceride, which is bad for purification of linoleic acid due to existence of monoglyceride and diglyceride; meanwhile, the technologies reported basically are at the level of chromatographic analysis with a small sample size and complicated elution system, falling short of requirements of production. These factors restrict the application of this technology in industrialized production and preparation of linoleic acid.

SUMMARY OF THE INVENTION

Given the above problems, this invention provides a method for efficient separation and purification of linoleate and preparation of CLA with vegetable oil, which mainly purifies linoleate with silver-based silica gel column and prepares CLA with purified linoleate, expanding sources of CLA, improving availability and added value of vegetable oil and realizing industrialized application of silver-loaded silica gel in purification of fatty acid ester.

To this end, this invention adopts the following technical scheme: a method for preparation of high-content CLA with vegetable oil, including the steps below:

1) Alcoholysis of vegetable oil: stir vegetable oil, catalyst and alcohol solution at 50-75° C. for 0.5-2 h, and wash them layer by layer to obtain the product;

2) Primary purification of alcoholysis product: conduct primary purification for the alcoholysis product by rectification or crystallization to remove low-boiling and high-melting impurities and obtain product of primary purification;

3) Repurification: weigh an appropriate amount of product of primary purification, add it into silver-based silica gel column after moderate dilution, adsorb it in static state for 5-30 min, conduct gradient elution with eluent, collect it section by section, remove the eluent, and measure the content of linoleate in each component;

4) Mix the linoleate, base catalyst and alcohol solvent, inject nitrogen, stir at 100-190° C. for 1-8 h, add water to terminate the reaction, cool to room temperature, dropwise add acid until pH reaches 1-3, layer, and wash upper-layer free fatty acid with 1-5% NaCl solution, 10-50% methanol aqueous solution and pure water in succession until it is clear and neutral to obtain high-content CLA.

Steps 1-3 of this invention are for separation and purification of linoleate: first convert glyceride of vegetable oil into corresponding methyl ester or ethyl ester for better separation and purification of linoleic acid; then conduct preliminary purification by dint of difference in boiling point and melting point of corresponding methyl ester or ethyl ester; finally elute and separate substances with different adsorption forces with mobile phase of certain polarity in light of different number of double bonds of each component and different binding forces for forming complex with silver ions to obtain high-content methyl linoleate or ethyl linoleate. Step 4 is for preparation of CLA. CLA of high conversion rate can be obtained by regulating the proportion of raw material, base catalyst and solvent, and reaction conditions.

Furthermore, in step 1), the vegetable oil is vegetable oil with linoleic acid content more than 20%, the catalyst is acid catalyst concentrated $H_2SO_4$, or basic catalyst NaOH, KOH, sodium methoxide or sodium ethoxide, the alcohol solution is methanol or ethanol, and the esterlysis product of vegetable oil is methyl ester or ethyl ester.

In addition, in step 3), the silver content of silver-based silica gel is 10%, and loading quantity of sample of silver-based silica gel column is not more than 40% of mass of silver-based silica gel.

Moreover, in step 3), the eluent is n-hexane, petroleum ether, n-heptane, ethyl acetate, chloroform, acetone, diethyl ether or MTBE or their combinations.

Furthermore, in step 4), the base catalyst is KOH, NaOH, sodium methoxide or sodium ethoxide; the alcohol solvent is monohydric alcohol, dihydric alcohol or trihydric alcohol, such as methanol, ethanol, glycol, glycerol, etc.; the acid is acetic acid, hydrochloric acid or sulfuric acid; the ratio of linoleate, base catalyst and alcohol solvent is 1 g:0.3-1.0 g:0.5-3 ml, and 1 g:0.3-0.8 g:0.5-2 ml is preferred.

Preparing high-content CLA with this invention solves the limitation of raw materials, greatly expands sources of CLA, changes the status quo of only using safflower oil and sunflower seed oil rich in linoleic acid as raw materials by applying most common vegetable oils, and increases added value of vegetable oil; products related to CLA can be prepared through follow-up operation of target product as needed, including free CLA and conjugated linoleate; the purification technology used in this invention achieves a good effect of separation, and can obtain products with content of CAL over 85% and even up to more than 95%, meeting needs of pharmaceutical, analysis, health food and other industries; the technological process of this invention is simple, and the solvents used can be recycled without environmental pollution, which makes industrialized production possible.

DETAIL DESCRIPTION OF THE INVENTION

This invention is further described below in line with specific implementation method.

Implementation Example 1

Methyl esterification: evenly mix 500 g soybean oil and 400 ml methanol, dropwise add 20 mL concentrated sulfuric acid, stir them at 75° C. for 0.5 h, keep them stationary for layering, wash the layer of methyl ester with 3% NaCl aqueous solution, and then wash the layer of methyl ester with 50-70° C. water until pH becomes 6-7 to obtain methyl soyate;

Preliminary purification of methyl ester: conduct preliminary purification for methyl ester through rectification at 150-170° C. with a vacuum degree of 20-100 Pa;

Purification of methyl linoleate: weigh 200 g of methyl ester after preliminary purification, dilute it with a little n-hexane, add it into a chromatographic column containing 1 kg of silver-based silica gel, elute it with a little n-hexane until it completely enters the chromatographic column, keep it stationary and adsorb it for 30 min, elute a column volume with 0, 10% and 20% n-hexane-ethyl acetate solvent systems as eluents, separately collect the part eluted with 10% eluent every 0.5 column volume and 0, 10% and 20% is volume concentration of ethyl acetate in n-hexane.

Preparation of CLA: add 30 g of KOH and 100 mL of glycol into the reaction vessel, heat and stir them for dissolution, add 100 g of methyl linoleate, heat them in N2 to 170° C., stir them for 3 h, add a little water, cool them to room temperature, dropwise add HCl to adjust pH to 1-3, stir them for 0.5 h, keep them stationary, separate the upper-layer oil phase product, wash it with 3% NaCl aqueous solution, 30% methanol aqueous solution and pure water three times respectively until pH=6-7, and obtain CLA with a purity of 88.7% and total recovery rate of 75%.

Implementation Example 2

Prepare methyl ester of sunflower seed oil with method of "methyl esterification" in implementation example 1, cool the methyl ester to 0° C. at 0.5-1.5° C./h while slowly stirring, keep it stationary overnight for crystallization, and filter it to obtain preliminarily purified methyl ester sample.

Weigh 150 g of methyl ester after preliminary purification, add it into a chromatographic column containing 0.8 kg of silver-based silica gel, elute it with a little petroleum ether until it completely enters the chromatographic column, keep it stationary and adsorb it for 15 min in a dark place, and elute a column volume with petroleum ether; elute it with 15% diethyl ether, separately collect every 0.5 column volume, and elute 1.5 column volume; remove eluent by rotary evaporation, dissolve it with 1.5 mL of n-hexane, and test it with GC to obtain a sample with linoleate purity of 95% and recovery rate of 60%.

Add 40 g of NaOH into a conical flask with 100 mL of glycol, heat and stir them for dissolution after adding $N_2$, add 50 g of methyl ester rich in linoleic acid, stir them for 4 h at 160° C., cool them to room temperature, add a little water, dropwise add concentrated hydrochloric acid until pH=1-3, keep them stationary for layering, and wash the upper layer with 4% NaCl aqueous solution, 50% methanol aqueous solution and pure water respectively until it become neutral to obtain CLA of content over 95%.

Implementation Example 3

Add 300 mL of anhydrous ethanol and 15 g of KOH into 200 g of soybean oil, keep them at 50° C. for 2 h, wash them with water after recovering ethanol, and obtain 180 g of ethyl ester of soybean oil after removing water.

Weigh 160 g of ethyl ester, dropwise add it into a chromatographic column containing 0.4 kg of silver-based silica gel after diluting it with n-hexane, adsorb it in static state for 5 min in a dark place, and use n-hexane—chloroform solvent system as mobile phase. Elute a column volume with n-hexane, 0.3 column volume with 15% chloroform, 0.7 column volume with 15% chloroform, and finally a column volume with 25% n-hexane, collect each part separately, and remove eluent by rotary evaporation to obtain ethyl linoleate of content up to 80% and recovery rate of 77%.

Conduct conjugation for the ethyl linoleate in glycerol solution with sodium methoxide as catalyst, ethyl ester: sodium methoxide:glycerol=1:0.3:0.5 (g:g:ml), dropwise add concentrated sulfuric acid after reacting at 190° C. for 1 h, and wash it with water to obtain free CLA of content more than 90%.

Add 30 g of free CLA into 7% sulfuric acid-methanol solution, inject $N_2$, stir them at 70° C. for 1 h, and wash each layer with water to obtain conjugated methyl linoleate of content over 90%.

Implementation Example 4

Stir at 60° C. for 1 h with cottonseed oil as raw material, KOH as catalyst and ethanol as reaction solvent, and obtain ethyl ester of cottonseed oil after layered washing and other treatments;

Preliminary purification of ethyl ester: conduct preliminary purification for ethyl ester through rectification at 150-170° C. with a vacuum degree of 20-100 Pa, crystallize the fraction at 5° C. overnight, and remove the lower-layer solid crystal through filtration;

Purification of ethyl linoleate: weigh 200 g of ethyl ester after preliminary purification, add the sample into a chromatographic column containing 1 kg of silver-based silica gel after diluting it with a little n-hexane, elute 0.5 column volume with n-hexane in a dark place, keep it stationary and adsorb it for 20 min, elute a column volume with 0, 2% and 8% acetone-n-hexane solvent systems respectively, separately collect every 0.5 column volume, and 0, 2% and 8% is volume concentration of acetone in n-hexane. Measure content of ethyl linoleate in each component with GC after removing solvent;

Preparation of CLA: add 50 g of NaOH and 200 mL of propylene glycol into a conical flask, add 100 g of ethyl linoleate after heating and stirring for full dissolution, heat them in N2 to 150° C., stir them for 5 h, dropwise add concentrated HCl until pH reaches 1-3, keep them stationary for layering, and wash the layer of fatty acid with 5% NaCl aqueous solution, 10% methanol aqueous solution and pure water in succession three times until pH becomes 6-7 to obtain CLA with a purity of 82% and total recovery rate of 80%.

Implementation Example 5

Prepare methyl ester of safflower oil through catalysis of NaOH, keep it stationary at 4° C. overnight for crystallization, and remove the crystal by rapid filtration; weigh 100 g of methyl ester after preliminary purification, add sample into a chromatographic column containing 0.35 kg of silver-based silica gel after dissolution with a little n-heptane, elute the methyl ester with n-heptane in a dark place until it completely enters the chromatographic column, keep it stationary and adsorb it for 30 min, and continue to elute a column volume with n-heptane; continuously elute with 10% MTBE, separately collect every 0.3 column volume, and elute 1.5 column volume; remove the eluent of each part respectively, and take samples for GC test to obtain samples with linoleate purity of 98% and recovery rate of 65%.

Conduct isomerization reaction for the high-content methyl linoleate to prepare free CLA, use methanol as solvent and NaOH as catalyst, inject $N_2$, dropwise add acetic acid after reacting at 100° C. for 8 h, and wash with water to obtain free CLA of content more than 95%.

What is claimed is:

1. A method for preparing high-content conjugated linoleic acid (CLA) through purification of vegetable oil comprising the following steps:
    step 1) stirring vegetable oil, catalyst and alcohol solution in a container at 50-75° C. for 0.5-2 h to get a mixture of solution, and wash the mixture of solution layer by layer to obtain a alcoholysis product;
    step 2) conducting primary purification for the alcoholysis product by rectification or crystallization to remove low-boiling and high-melting impurities and obtain primary purified alcoholysis product;
    step 3) weigh out an appropriate amount of primary purified alcoholysis product, add it into silver-based silicagel column after moderate dilution, adsorb it in static state for 5-30 min in a dark place, conduct gradient elution with eluent, collect it section by section, remove the eluent, and measure a content of linoleate in each component gotten from each section;
    step 4) mixing the linoleate, base catalyst and alcohol solvent together, inject nitrogen in to the mixture thereof, stir the mixture at 100-190° C. for 1-8 h, add water to terminate the reaction and cool to room temperature, dropwise add acid into the mixture until pH reaches 1-3, layer, and wash a upper-layer of free fatty acid with 1-5% NaCl solution, 10-50% methanol aqueous solution and pure water in succession until it is clear and neutral to obtain high-content CLA.

2. The method for preparing high-content conjugated linoleic acid (CLA) through purification of vegetable oil of claim 1, wherein in step 1), the vegetable oil is vegetable oil with linoleic acid content more than 20%, the catalyst is acid catalyst concentrated $H_2SO_4$, or basic catalyst NaOH, KOH, sodium methoxide or sodium ethoxide, the alcohol solution is methanol or ethanol, and the alcoholysis product of vegetable oil is methyl ester or ethyl ester.

3. The method for preparing high-content conjugated linoleic acid (CLA) through purification of vegetable oil of claim 1, wherein in step 3), the silver content of silver-based silica gel is 10%, and loading quantity of sample of silver-based silica gel column is not more than 40% of mass of silver-based silica gel.

4. The method for preparing high-content conjugated linoleic acid (CLA) through purification of vegetable oil of claim 1, wherein in step 3), the eluent is n-hexane, petroleum ether, n-heptane, ethyl acetate, chloroform, acetone, diethyl ether or MTBE or their combinations.

5. The method for preparing high-content conjugated linoleic acid (CLA) through purification of vegetable oil of claim 1, wherein in step 4), the base catalyst is KOH, NaOH, sodium methoxide or sodium ethoxide; the alcohol solvent is monohydric alcohol, dihydric alcohol or trihydric alcohol; the acid is acetic acid, hydrochloric acid or sulfuric acid; a ratio of linoleate, base catalyst and alcohol solvent is 1 g: 0.3-1.0 g: 0.5-3 ml.

6. The method for preparing high-content conjugated linoleic acid (CLA) through purification of vegetable oil of claim 5, wherein in step 4), the ratio of linoleate, base catalyst and alcohol solvent is 1 g:0.3-0.8 g:0.5-2 ml.

\* \* \* \* \*